United States Patent [19]

Shum

[11] Patent Number: 5,780,655
[45] Date of Patent: Jul. 14, 1998

[54] EPOXIDATION PROCESS USING A PHOSPHATE-STABILIZED PEROXOTUNGSTATE COMPOUND AS CATALYST

[75] Inventor: Wilfred Po-sum Shum, West Chester, Pa.

[73] Assignee: ARCO Chemical Technology, L.P., Greenville, Del.

[21] Appl. No.: 850,983

[22] Filed: May 5, 1997

[51] Int. Cl.[6] ................................. C07D 301/12
[52] U.S. Cl. ................................................ 549/531
[58] Field of Search ............................................ 549/531

[56] References Cited

U.S. PATENT DOCUMENTS 4,562,276   12/1985   Venturello et al. ................ 556/20
4,595,671   6/1986   Venturello et al. ................ 502/159
5,274,140   12/1993   Venturello et al. ................ 549/531
5,324,849   6/1994   Bonsignore et al. ............... 556/14

FOREIGN PATENT DOCUMENTS 19533331   3/1997   Germany.

OTHER PUBLICATIONS

Salles et al., Inorg. Chem. 33, 871–878 (1994).

Primary Examiner—Ba K. Trinh
Attorney, Agent, or Firm—Stephen D. Harper

[57] ABSTRACT

Olefins are selectively converted to epoxides using hydrogen peroxide as oxidant in a single liquid phase reaction system characterized by a liquid phase comprised predominantly of an organic solvent. The reaction is catalyzed by a compound comprised of a phosphate-stabilized peroxotungstate species having a W:P atomic ratio of 2:1.

20 Claims, No Drawings

5,780,655

EPOXIDATION PROCESS USING A PHOSPHATE-STABILIZED PEROXOTUNGSTATE COMPOUND AS CATALYST

FIELD OF THE INVENTION

This invention pertains to methods of converting olefins to epoxides in a single liquid phase using hydrogen peroxide and a catalyst in salt or acid form comprising a species corresponding to $|PW_2O_{13}(OH)|^{-2}$.

BACKGROUND OF THE INVENTION

U.S. Pat. No. 5,274,140 discloses a process for olefin epoxidation by reaction with hydrogen peroxide according to a double phase technique (i.e., a biphasic reaction system containing both an aqueous phase and an organic phase). The catalyst system consists of a first component which is at least one element selected from W, Mo, V or a derivative thereof and a second component which is at least one derivative selected from the derivatives of P and As. The mutual atomic ratio of the catalyst components is between 12 and 0.1, but preferably is between 1.5 and 0.25.

U.S. Pat. Nos. 4,562,276 and 4,595,671 describe epoxidation catalysts for olefinic compounds, both in a homogeneous aqueous phase as well as in a heterogeneous phase. The catalysts correspond to the formula $Q_3XW_4O_{24-2n}$ wherein Q represents a cation of an anionic salt, X is either P or As, while n=0, 1 or 2. The atomic ratio of W:P, where X=P, thus must be 4. The use of such compositions in an epoxidation wherein the reactants are maintained in a single substantially organic phase is not disclosed.

U.S. Pat. No. 5,324,849 teaches a class of compounds based on tungsten and diphosphonic acids which contain active oxygen atoms and cationic groups derived from onium salts. Such compounds are said to catalyze olefin oxidation reactions in double phase reaction systems containing both an organic phase and an aqueous phase. The compounds contain two phosphorus atoms and five tungsten atoms and thus have a W:P atomic ratio of 5:2.

Biphasic reaction systems of the type described in the aforementioned patents have a number of disadvantages which limit their usefulness in large scale commercial practice, however. The need to use a phase transfer agent contributes significantly to the cost of operation. Mass transfer problems are frequently encountered, particularly for relatively volatile olefins such as propylene. Additionally, there are considerable engineering difficulties associated with operating two phase reactors and phase separators. Thus, there is a need to develop active catalysts capable of providing high selectivity to epoxide during operation of a single phase epoxidation process.

SUMMARY OF THE INVENTION

This invention provides a process for epoxidizing an olefin comprising contacting the olefin with hydrogen peroxide in a substantially organic single liquid phase reaction system in the presence of a catalytically effective amount of a compound in salt or acid form comprising a species corresponding to $|PW_2O_{13}(OH)|^{-2}$ for a time and at a temperature effective to form an epoxide corresponding to the olefin.

DETAILED DESCRIPTION OF THE INVENTION

The compounds utilized as catalyst in the epoxidation process of this invention are comprised of a species corresponding to the empirical formula $|PW_2O_{13}(OH)|^{-2}$. This species is characterized by having a W:P atomic ratio of 2:1 and may be described as a phosphate-stabilized peroxotungstate. The compound may be in acid or salt form. The cationic portion of the compound is not critical and may be any positively charged species in an amount sufficient to provide overall neutrality of the compound. In one particularly preferred embodiment of the invention, however, the compound has the empirical formula $Y|PW_2O_{13}(OH)|$ wherein Y is H+, alkyl ammonium or combinations thereof, x=0 when Y is a monocation, and x=1 when Y is a dication. The identity of Y may be suitably varied to impart the desired solubility characteristics to the compound. Alkyl ammonium cations are generally selected when solubilization of the salt in the single liquid phase reaction system is desired. Suitable alkyl ammonium species are those positively charged nitrogen species having at least one alkyl group attached to nitrogen. More preferably, Y is a quaternary ammonium species corresponding to $NR_1R_2R_3R_4$ wherein $R_1$, $R_2$, $R_3$ and $R_4$ are the same or different and are selected from $C_1-C_{24}$ alkyl groups. Y may also be a diquaternary ammonium species containing two tetrasubstituted nitrogen atoms. The species providing the counter cations to $|PW_2O_{13}(OH)|^{-2}$ may alternatively be immobilized in a polymeric or inorganic matrix which is insoluble in the substantially organic single liquid phase reaction system of this invention. For example, a layered double hydroxide of the type described in *Tetrahedron Letters*, 8557 (1996) may be adapted for use as a support with the phosphate-stabilized peroxotungstate compounds described herein. Ion exchange resins having quaternary ammonium functionality such as Amberlite IRA-400(Cl) may also be utilized.

The aforedescribed phosphate-stabilized peroxotungstate compounds are known in the art and may be synthesized by any suitable procedure such as, for example, the methods described in Salles et al., *Inorganic Chemistry* 33, 871–878 (1994).

For example, tungstic acid ("$H_2WO_4$") is combined with aqueous hydrogen peroxide and then phosphoric acid ($H_3PO_4$) to yield a precursor. Alternatively, $H_3|PW_{12}O_{40}|$ • y $H_2O$ (available from commercial sources such as Janssen and Aldrich Chemical Company) is treated with phosphoric acid, then hydrogen peroxide, to yield the precursor. The precursor is thereafter reacted with a compound or substance capable of providing the desired cation(s) "Y" such as an alkyl ammonium halide or the like. Such procedures will yield the compound in salt form. The acid form may be generated by calcination of the salt form of the compound under conditions effective to remove the alkyl ammonium. Heating the salt form of the compound at a temperature in excess of 400° C. (preferably, no greater than 800° C.) for a time of from about 0.5 hours to 24 hours is generally effective for this purpose. Calcination in the presence of oxygen is typically preferred.

Other materials having catalytic activity in olefin epoxidation may also be present in addition to the aforedescribed phosphate-stabilized peroxotungstate compounds. For example, the catalysts containing phosphorus and tungsten described in U.S. Pat. Nos. 5,274,140, 4,562,276, 4,595,671 and 5,324,849 may be utilized in admixture with the catalyst required by the process of the present invention.

The olefins which may be subjected to the epoxidation reaction include, but are not limited to, unsaturated alkyl, alicyclic, alkylaryl hydrocarbons such as ethylene, propylene, butenes, pentenes, and in general linear or branched mono-and di-olefins having up to 20 carbon atoms, cyclohexene, norborene, limonene, camphene, vinyl cyclohexene, styrene, indene, stilbene and the like; unsaturated alkyl halides such as allyl chloride; unsaturated acids and their esters such as acrylic acid, methacrylic acid, crotonic acid, oleic acid, methyl acrylate, and the like; unsaturated alcohols and their esters such as allyl alcohol, methallyl alcohol, and the like; unsaturated aldehydes; unsaturated ketones and the like. The olefin may be substituted with any substituent which does not interfere with the desired epoxidation reaction such as, for example, hydroxy, halogen, nitro, alkoxy, amine, carbonyl, carboxylic, ester, amide, or nitrile groups, polyolefins such as dienes (e.g., 1,4-butadiene), trienes, either conjugated or not, may also be successfully utilized. Acyclic alkenes containing from 3 to 10 carbon atoms are most preferred for use.

The epoxidation process of this invention is characterized by having a single liquid phase. That is, separate organic and aqueous layers are not present. Moreover, while the single liquid phase may contain water, the reaction system is comprised predominantly (e.g., greater than 50 weight percent) of one or more organic solvents (i.e., the liquid phase is "substantially organic"). While the olefin being epoxidized may function as a solvent when used in excess relative to hydrogen peroxide, in preferred embodiments an additional organic solvent is present. The organic solvent is advantageously selected such that the hydrogen peroxide, water (if present), and olefin form a single homogeneous liquid phase when combined with the organic solvent under the epoxidation conditions. Generally speaking, relatively polar organic solvents which are miscible with water and/or hydrogen peroxide, at least to some degree, are preferred for use. Such solvents include, for example, $C_1$-$C_5$ alcohols (e.g., methanol, ethanol, isopropanol, t-butyl alcohol, t-amyl alcohol, fluorinated alcohols), $C_2$-$C_3$ nitriles (e.g., acetonitrile), and $C_2$-$C_6$ ethers (e.g., tetrahydrofuran, glyme, dioxane, glycol ethers). The solvent is preferably a liquid under the epoxidation conditions and should be non-reactive.

The epoxidation temperature is not critical, with the optimum temperature being influenced by, among other factors, the reactivity and nature of the olefin. Typically, however, temperatures between 0° C. and 125° C. are sufficient to achieve selective conversion of blefin to epoxide. Reaction times of from a few minutes to a few hours are generally utilized. Pressure also is not critical, although with more volatile olefins such as propylene it will be desirable to use a sufficiently high pressure to maintain the desired concentration of olefin in the liquid phase where epoxidation is taking place. Pressures of from atmospheric to 100 atmospheres will generally be suitable for operation of the present process.

The catalyst is used in quantities between 0.0001 and 1 g/atom of tungsten per 1 mol of hydrogen peroxide, more preferably between 0.005 and 0.05 g/atom W per 1 mol $H_2O_2$.

The concentration of the olefin in the single phase liquid reaction system is not critical, with concentrations of from 1% to 50% by weight typically being selected for practical reasons. Similarly, the concentration of hydrogen peroxide is not regarded as critical. One advantage of the process of this invention is that it is capable of providing high selectivity to epoxide even with the $H_2O_2$ concentration is relatively low (e.g., 1 to 15 weight percent based on the total weight of the liquid phase). Higher or lower concentrations may be utilized, however, if so desired. The hydrogen peroxide may be derived from any suitable source such as, for example, air oxidation of an anthra-quinone, secondary alcohol, or the like.

The hydrogen peroxide may be either introduced as such or produced by substances capable of generating hydrogen peroxide under the reaction conditions. For example, hydrogen peroxide may be generated in situ by reaction of oxygen and hydrogen in the presence of a suitable catalyst.

The olefin and hydrogen peroxide are used in substantially equimolar ratios. An excess or lack of excess with respect to one or the other of the reactants does not interfere with the desired epoxidation. While olefin to hydrogen peroxide mole ratios of between 0.1:1 and 50:1 may be utilized, ratios between 1:1 and 10:1 are generally preferred.

EXAMPLES

The procedure described in Salles et al., *Inorg. Chem.* 33, 871–878(1994) was used to prepare the salt corresponding to (n-Bu$_4$N)$_2$|PW$_2$O$_{13}$(OH)|. Epoxidation of a variety of olefins using hydrogen peroxide was generally performed using the following proportions of reagents: 18 mmol olefin, 5% hydrogen peroxide and 5% water in an organic solvent (12 g, 18 mmol $H_2O_2$), 0.09 g (0.08 mmol) of the salt as catalyst. Where propylene was the olefin, the following proportions were utilized: 14 g (330 mmol) propylene, 5% $H_2O_2$ and 5% $H_2O$ in acetonitrile (42 g; 62 mmol $H_2O_2$), 0.5 g (0.45 mmol) salt as catalyst. The results obtained are shown in Table 1. The % epoxide yield is based on hydrogen peroxide conversion.

These results demonstrate that remarkably high selectivity to epoxide is achieved by the process of the invention under mild reaction conditions in both protic and aprotic solvents. This was quite surprising in view of the fact that water was present in the same liquid phase as the olefin being reacted. Normally, water will either deactivate epoxidation catalysts or react with epoxide to generate ring-opened by-products, thereby substantially reducing the yield of the desired epoxide.

TABLE I

| Olefin | Organic Solvent | Temp., °C. | Run Time, hr. | $H_2O_2$ Conv., % | Epoxide Selectivity[1], % |
|---|---|---|---|---|---|
| 1-hexene | acetonitrile | 60 | 2 | 15 | 87 |
| trans-2-hexene | acetonitrile | 60 | 2 | 25 | 88 |
| cis-2-pentene | acetonitrile | 60 | 1 | 29 | 86 |
| cis-2-pentene | n-butanol | 60 | 1.1 | 52 | 82 |
| cis-2-pentene | t-butyl alcohol | 60 | 1.7 | 35 | 83 |
| cis-2-pentene | 1,4-dioxane | 60 | 1.1 | 25 | 88 |
| crotyl alcohol | acetonitrile | 60 | 1 | 46 | 89 |
| propylene | acetonitrile | 76 | 2.5 | 52 | 77 |
| methallyl alcohol | acetonitrile | 60 | 1.1 | 31 | 85 |
| trans-2-hexen-1-ol | acetonitrile | 60 | 1.7 | 50 | 88 |
| cyclohexene | acetonitrile | 60 | 1.1 | 47 | 90 |
| propylene | 1,4-dioxane | 77 | 2.5 | 76 | 76 |
| propylene | t-butyl alcohol | 78 | 2.5 | 54 | 77 |
| propylene | n-butanol | 72 | 2.5 | 91 | 60 |

[1]based on hydrogen peroxide conversion

The catalytic activity of the acid form of a phosphate-stabilized peroxotungstate compound was investigated as follows. A 1 g sample of (n-Bu$_4$N)$_2$ |PW$_2$O$_{13}$(OH)| was placed in an oven at 500° C. under a slow flow of air for 5 hours. Elemental analysis and IR spectroscopy indicated that all of the tetrabutyl ammonium counterion had been removed. The solids were dissolved into 55 g of a 5% $H_2O_2$ solution (in acetonitrile or 1,4-dioxane) by stirring at 60° C. for 2 hours. The resulting catalyst solution was used to epoxidize propylene in acetonitrile under the conditions previously described. After 2.5 hours at 65° C. 90% conversion of hydrogen peroxide and 64% selectivity to propylene oxide were observed.

We claim:

1. An epoxidation process comprising contacting an olefin with hydrogen peroxide in a substantially organic single liquid phase reaction system in the presence of a catalytically effective amount of a compound in salt or acid form comprising a species corresponding to $[PW_2O_{13}(OH)]^{-2}$ for a time and at a temperature effective to form an epoxide corresponding to the olefin.

2. The epoxidation process of claim 1 wherein the substantially organic single liquid phase reaction system is comprised of less than 10 weight % water.

3. The epoxidation process of claim 1 wherein the single liquid phase reaction system is comprised of an organic solvent selected from the group consisting of $C_1$-$C_4$ alcohols, $C_2$-$C_3$ nitriles, $C_2$-$C_6$ ethers, and mixtures thereof.

4. The epoxidation process of claim 1 wherein the compound additionally is comprised of a cation selected from the group consisting of $H^+$, alkyl ammonium, and combinations thereof.

5. The epoxidation process of claim 1 wherein the olefin is a $C_3$-$C_{10}$ acyclic alkene.

6. The epoxidation process of claim 1 wherein the temperature is from 0° C. to 125° C.

7. The epoxidation process of claim 1 wherein the compound is soluble in the substantially organic single liquid phase reaction system.

8. The epoxidation process of claim 1 wherein the compound is immobilized in a polymeric or inorganic matrix.

9. An epoxidation process comprising contacting a $C_3$-$C_{10}$ acyclic alkene with hydrogen peroxide in a single liquid phase reaction system comprised of less than 10 weight % water and an organic solvent in the presence of a catalytically effective amount of a compound having an empirical formula $Y_{2-x}$ $[PW_2O_{13}(OH)]$ wherein Y is $H^+$, alkyl ammonium, or combinations thereof, x=0 when Y is a monocation, and x=1 when Y is a dication at a temperature of 0° C. to 125° C. for a time effective to form an epoxide corresponding to the $C_3$-$C_{10}$ acyclic alkene.

10. The epoxidation process of claim 9 wherein the $C_2$-$C_{10}$ mono-olefin is propylene.

11. The epoxidation process of claim 9 wherein the organic solvent is selected from the group consisting of $C_2$-$C_4$ alcohols, $C_2$-$C_3$ nitriles, $C_2$-$C_6$ ethers and mixtures thereof.

12. The epoxidation process of claim 9 wherein Y is an alkylammonium cation corresponding to $NR_1R_2R_3R_4$ wherein $R_1$, $R_2$, $R_3$ and $R_4$ are the same or different and are selected from $C_1$-$C_{24}$ alkyl groups.

13. The epoxidation process of claim 9 wherein the compound is formed by reacting $H_3PW_{12}O_{40}$, $H_3PO_4$ and hydrogen peroxide to form a precursor and reacting the precursor with an alkyl ammonium halide.

14. The epoxidation process of claim 9 wherein the compound is formed by reacting tungstic acid, hydrogen peroxide, and $H_3PO_4$ to form a precursor and reacting the precursor with an alkyl ammonium halide.

15. The epoxidation process of claim 9 wherein the compound is formed by reacting $H_3PW_{12}O_{40}$, $H_3PO_4$ and hydrogen peroxide to form a precursor, reacting the precursor with an alkyl ammonium halide to form the compound in salt form, and calcining the compound to provide the compound in acid form.

16. The epoxidation process of claim 9 wherein the compound is formed by reacting tungstic acid, hydrogen peroxide, and $H_3PO_4$ to form a precursor, reacting the precursor with an alkyl ammonium halide to form the compound in salt form, and calcining the compound to provide the compound in acid form.

17. The epoxidation process of claim 9 wherein water is removed from the single liquid phase reaction system during epoxidation.

18. The epoxidation process of claim 9 wherein the $C_3$-$C_{10}$ acyclic alkene is propylene.

19. The epoxidation process of claim 9 wherein the amount of the compound is from 0.0001 to 1 g/atom of tungsten per mole of hydrogen peroxide.

20. The epoxidation process of claim 9 wherein the organic solvent is selected from the group consisting of methanol, ethanol, n-propanol, isopropanol, n-butanol, sec-butanol, t-butanol, acetonitrile, 1,4-dioxane, tetrahydrofuran, glyme, and mixtures thereof.

* * * * *